(12) United States Patent
Goto et al.

(10) Patent No.: US 11,055,825 B2
(45) Date of Patent: Jul. 6, 2021

(54) MEDICAL IMAGE PROCESSING DEVICE AND X-RAY CT DEVICE PROVIDED WITH SAME, AND MEDICAL IMAGE PROCESSING METHOD

(71) Applicant: Hitachi, Ltd., Tokyo (JP)

(72) Inventors: Taiga Goto, Tokyo (JP); Hisashi Takahashi, Tokyo (JP)

(73) Assignee: Hitachi, Ltd., Tokyo (JP)

(*) Notice: Subject to any disclaimer, the term of this patent is extended or adjusted under 35 U.S.C. 154(b) by 183 days.

(21) Appl. No.: 16/464,322

(22) PCT Filed: Dec. 1, 2017

(86) PCT No.: PCT/JP2017/043353
§ 371 (c)(1),
(2) Date: May 28, 2019

(87) PCT Pub. No.: WO2018/116791
PCT Pub. Date: Jun. 28, 2018

(65) Prior Publication Data
US 2021/0110516 A1    Apr. 15, 2021

(30) Foreign Application Priority Data

Dec. 22, 2016 (JP) .............................. JP2016-248929

(51) Int. Cl.
*G06T 5/00* (2006.01)
*A61B 6/02* (2006.01)
(Continued)

(52) U.S. Cl.
CPC .............. *G06T 5/002* (2013.01); *A61B 6/027* (2013.01); *A61B 6/032* (2013.01); *A61B 6/5264* (2013.01);
(Continued)

(58) Field of Classification Search
CPC . G06T 5/002; G06T 5/50; G06T 2207/10081; G06T 2207/20004;
(Continued)

(56) References Cited

U.S. PATENT DOCUMENTS 5,473,655 A * 12/1995 Hu ...................... G01N 23/046
378/4
6,459,756 B1 * 10/2002 Tam ...................... G06T 11/005
378/15
(Continued)

FOREIGN PATENT DOCUMENTS

CN       1729936 A    2/2006
CN     102576468 A    7/2012
(Continued)

OTHER PUBLICATIONS

International Preliminary Report on Patentability for the International Patent Application No. PCT/JP2017/043353, dated Jun. 25, 2019, 6 pages.
(Continued)

*Primary Examiner* — Vu Le
*Assistant Examiner* — Julius Chenjun Chai
(74) *Attorney, Agent, or Firm* — Baker Botts L.L.P.

(57) ABSTRACT

Even a windmill artifact including a high-frequency component in a plane perpendicular to a rotation axis can be reduced and a boundary of an organ can be made to be clear to maintain the contrast.
The invention relates to a medical image processing device and includes an image acquiring unit that acquires a 3D volumetric image, a Z high-frequency image generating unit that generates a Z high-frequency image which is a high-frequency component in a rotation axis direction from the 3D volumetric image, an organ component extracting unit that extracts an organ component from the Z high-frequency
(Continued)

image, an artifact component extracting unit that extracts an artifact component on the basis of the Z high-frequency image and the organ component, and a corrected image generating unit that generates a corrected image by subtracting the artifact component from the 3D volumetric image.

13 Claims, 9 Drawing Sheets

(51) Int. Cl.
  *A61B 6/03* (2006.01)
  *A61B 6/00* (2006.01)
  *G06T 5/50* (2006.01)
(52) U.S. Cl.
  CPC ...... *G06T 5/50* (2013.01); *G06T 2207/10081* (2013.01); *G06T 2207/20004* (2013.01); *G06T 2207/20224* (2013.01); *G06T 2207/30004* (2013.01)

(58) Field of Classification Search
  CPC . G06T 2207/20224; G06T 2207/30004; A61B 6/027; A61B 6/032; A61B 6/5264
  See application file for complete search history.

(56) References Cited

U.S. PATENT DOCUMENTS

| 8,938,108 | B2 | 6/2015 | Brown et al. |
| 2006/0029285 | A1* | 2/2006 | Hein ................... G06T 5/002 382/260 |
| 2012/0183194 | A1* | 7/2012 | Brown ................. G06T 11/008 382/131 |
| 2013/0170609 | A1 | 7/2013 | Nett et al. |
| 2016/0086319 | A1 | 3/2016 | Honda et al. |
| 2016/0364856 | A1 | 12/2016 | Zheng et al. |
| 2017/0071554 | A1* | 3/2017 | Fukuda ............... G06T 11/006 |
| 2018/0350113 | A1* | 12/2018 | Goto .................. G06T 11/008 |

FOREIGN PATENT DOCUMENTS

| JP | 2006043431 A | 2/2006 |
| JP | 2013-506520 A | 2/2013 |
| JP | 2013506520 A | 2/2013 |
| JP | 2014-233608 A | 12/2014 |
| JP | 2014233608 A | 12/2014 |
| WO | 2011042821 A1 | 4/2011 |
| WO | 2014/196608 A1 | 12/2014 |

OTHER PUBLICATIONS

International Search Report and Written Opinion issued in international application No. PCT/JP2017/043353 dated Jun. 28, 2018, 9 pages.

* cited by examiner

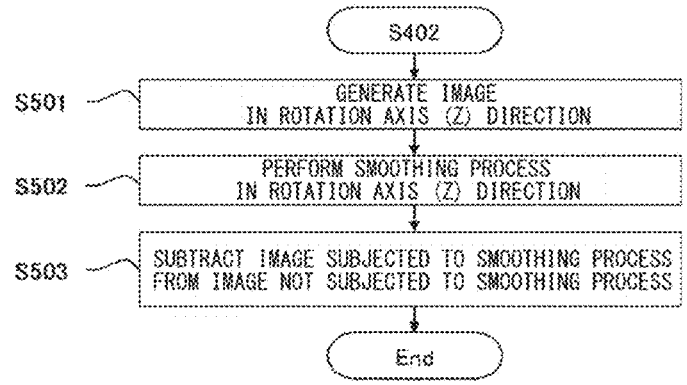
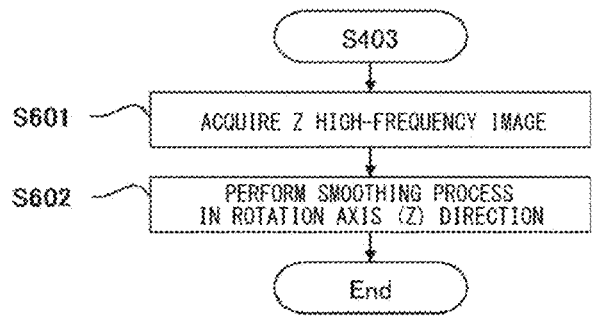
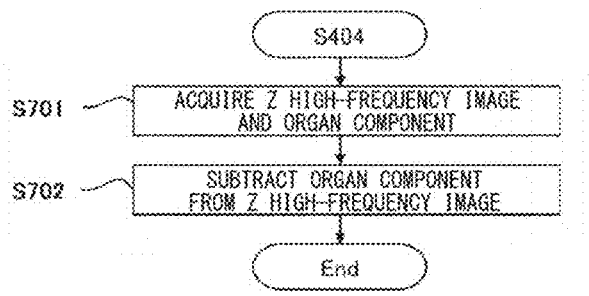

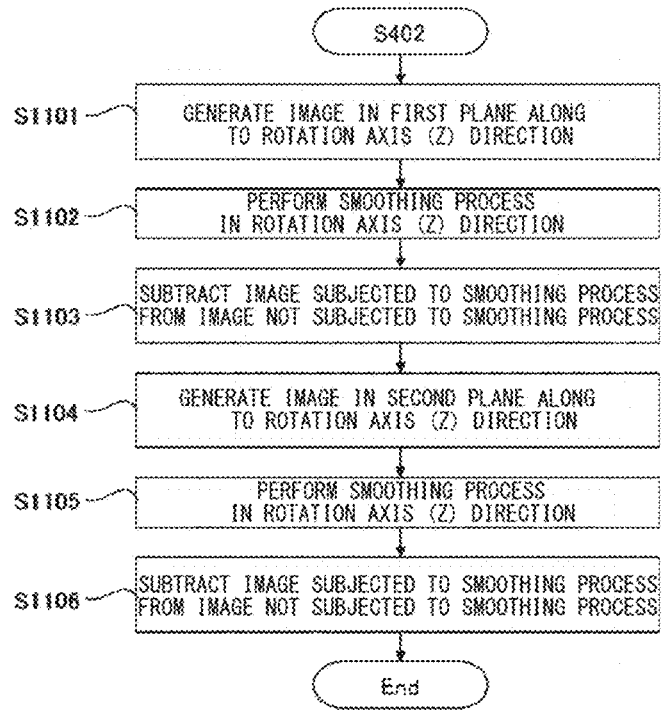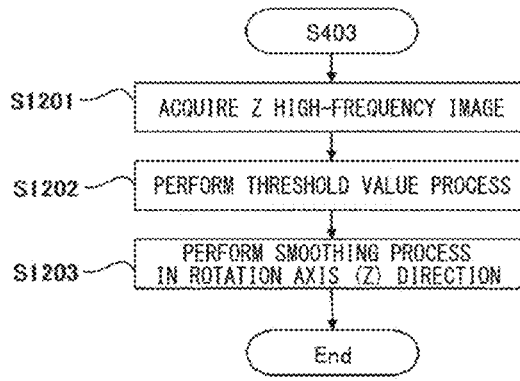

MEDICAL IMAGE PROCESSING DEVICE AND X-RAY CT DEVICE PROVIDED WITH SAME, AND MEDICAL IMAGE PROCESSING METHOD

CROSS-REFERENCE TO RELATED APPLICATIONS

This application is a national phase claiming the benefit of and priority to International Patent Application No. PCT/JP2017/043353, entitled "MEDICAL IMAGE PROCESSING DEVICE AND X-RAY CT DEVICE PROVIDED WITH SAME, AND MEDICAL IMAGE PROCESSING METHOD", filed Dec. 1, 2017, which claims priority to Japanese Patent Application No. 2016-248929, filed Dec. 22, 2016, which are hereby incorporated by reference in their entireties.

TECHNICAL FIELD

The present invention relates to a medical image processing device and a medical image processing method that process a tomographic image which is acquired by an X-ray computed tomography (CT) device and particularly to a technique of reducing a windmill artifact which is generated due to under-sampling in a rotation axis direction of an X-ray CT device.

BACKGROUND ART

An X-ray CT device is a device that reconstructs tomographic images on the basis of projection data from various angles which are acquired by radiating X-rays from the surrounding of an examinee and displays the reconstructed tomographic images. The tomographic images displayed in the X-ray CT device are images of a shape of organs in the examinee and are used as medical images for image diagnosis.

With recent advancement in helical scan of acquiring projection data by moving an examinee in a rotation axis direction while rotating an X-ray source and an X-ray detector or a multi-slice CT device in which the number of rows of the X-ray detector has been increased in the rotation axis direction, an increase in an imaging speed has been achieved. In helical scan in a multi-slice CT device, a windmill artifact may be generated due to under-sampling in the rotation axis direction and such an artifact hinders image diagnosis.

An example of a method of reducing a windmill artifact is disclosed in Patent Document 1. This method is a method based on the fact that a windmill artifact includes a high-frequency component in a rotation axis direction and a low-frequency component in a plane perpendicular to a rotation axis and has the following process flow:

(1) generating image data in the rotation axis direction from 3D volumetric image data including a windmill artifact;

(2) removing noise from image data in the rotation axis direction;

(3) subtracting image data in the rotation axis direction from which noise has been removed from the image data in the rotation axis direction;

(4) replacing the image data acquired by subtraction with the image data in the rotation axis direction;

(5) generating image data in a plane perpendicular to the rotation axis from the image data acquired by the replacement;

(6) removing noise from the image data in the plane perpendicular to the rotation axis; and (7) subtracting image data in the plane perpendicular to the rotation axis from which noise has been removed from the 3D volumetric image data.

CITATION LIST

Patent Document

Patent Document 1: Japanese Patent No. 5711241

SUMMARY OF THE INVENTION

Technical Problem

However, in the method disclosed in Patent Document 1, a windmill artifact in the plane perpendicular to the rotation axis can be reduced to a certain extent, but a windmill artifact including a high-frequency component cannot be sufficiently reduced and a boundary of an organ can be made to be unclear to cause a decrease in contrast.

Therefore, an objective of the invention is to provide a medical image processing device and a medical image processing method that can reduce a windmill artifact including a high-frequency component in a plane perpendicular to a rotation axis and make a boundary of an organ clear to maintain the contrast.

Solution to Problem

In order to achieve the above-mentioned objective, the invention is characterized in that an organ component is extracted from a high-frequency component in a rotation axis direction and a windmill artifact is extracted by removing the extracted organ component from the high-frequency component.

Specifically, according to the invention, there is provided a medical image processing device includes: an image acquiring unit that acquires a 3D volumetric image; a Z high-frequency image generating unit that generates a Z high-frequency image which is a high-frequency component in a rotation axis direction from the 3D volumetric image; an organ component extracting unit that extracts an organ component from the Z high-frequency image; an artifact component extracting unit that extracts an artifact component on the basis of the Z high-frequency image and the organ component; and a corrected image generating unit that generates a corrected image by subtracting the artifact component from the 3D volumetric image.

According to the invention, there is also provided a medical image processing method including: an image acquiring step of acquiring a 3D volumetric image; a Z high-frequency image generating step of generating a Z high-frequency image which is a high-frequency component in a rotation axis direction from the 3D volumetric image; an organ component extracting step of extracting an organ component from the Z high-frequency image; an artifact component extracting step of extracting an artifact component on the basis of the Z high-frequency image and the organ component; and a corrected image generating step of generating a corrected image by subtracting the artifact component from the 3D volumetric image.

Advantageous Effects of the Invention

According to the invention, it is possible to provide a medical image processing device and a medical image processing method that can reduce a windmill artifact including a high-frequency component in a plane perpendicular to a rotation axis and make a boundary of an organ clear to maintain the contrast.

BRIEF DESCRIPTION OF THE DRAWINGS

FIG. 5 is a diagram illustrating a process flow of S402 in the first embodiment.

FIG. 6 is a diagram illustrating a process flow of S403 in the first embodiment.

FIG. 7 is a diagram illustrating a process flow of S404 in the first embodiment.

FIG. 11 is a diagram illustrating a process flow of S402 in a second embodiment.

FIG. 12 is a diagram illustrating a process flow of S403 in a third embodiment.

MODE FOR CARRYING OUT THE INVENTION

First Embodiment

Figure 1:
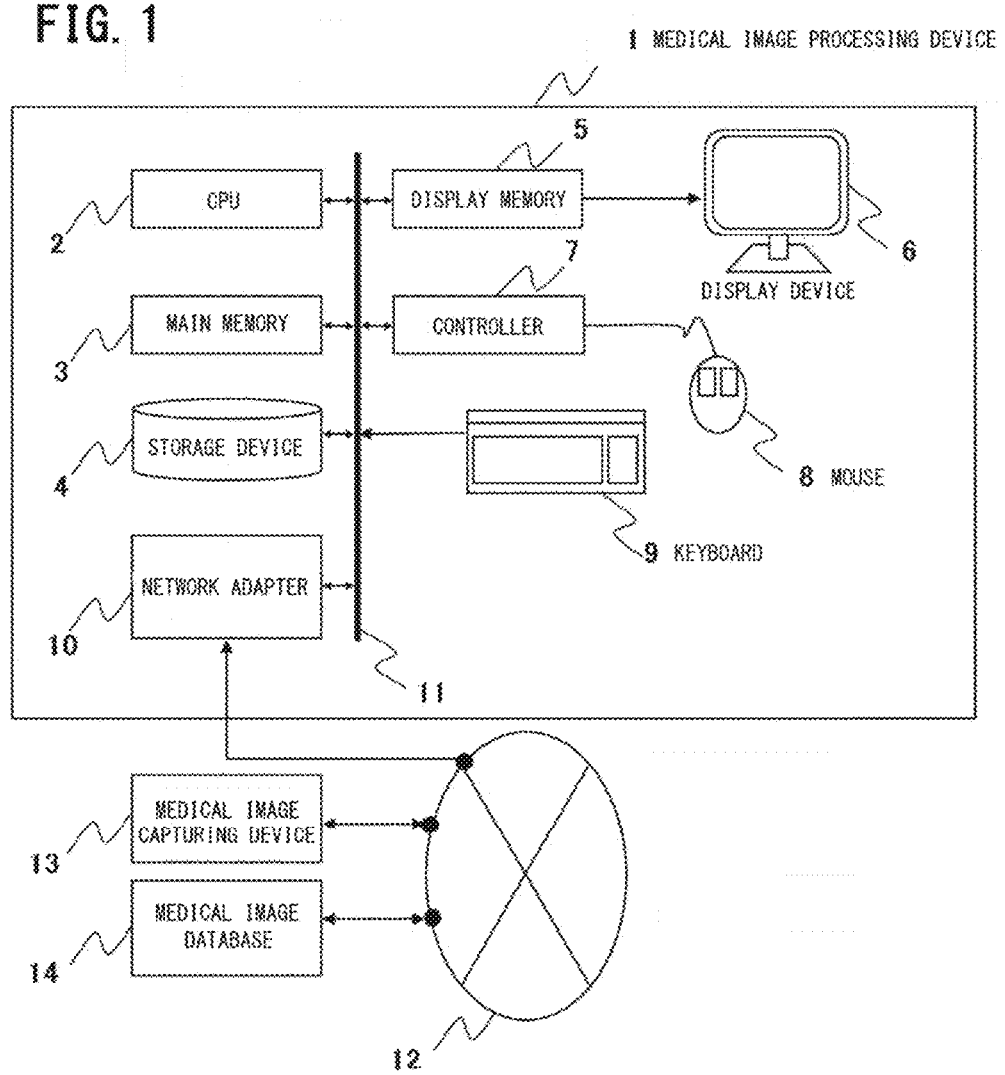
FIG. 1 is a diagram illustrating the whole configuration of a medical image processing device 1 according to the invention.

Hereinafter, exemplary embodiments of a medical image processing device and a medical image processing method according to the invention will be described with reference to the accompanying drawings. In the following description and the accompanying drawings, elements having the same functional configurations will be referred to by the same reference numerals and description thereof will not be repeated.

FIG. 1 is a diagram illustrating a hardware configuration of a medical image processing device 1. The medical image processing device 1 has a configuration in which a central processing unit (CPU) 2, a main memory 3, a storage device 4, a display memory 5, a display device 6, a controller 7 connected to a mouse 8, a keyboard 9, and a network adapter 10 are connected to each other via a system bus 11 such that a signal can be transmitted and received therebetween. The medical image processing device 1 is connected to a medical image capturing device 13 or a medical image database 14 via a network 12 such that a signal can be transmitted and received therebetween. Here, "such that a signal can be transmitted and received therebetween" refers to a state in which a signal can be transmitted and received to each other or from one to the other regardless of in which of electrical, optical, wired, or wireless manner communication is performed.

The CPU 2 is a device that controls operations of the constituent units. The CPU 2 loads a program stored in the storage device 4 or data required for execution of the program from the main memory 3 and executes the loaded program. The storage device 4 is a device that stores the program which is executed by the CPU 2 or data which is required for execution of the program and a specific example thereof is a hard disk. A variety of data is transmitted and received via the network 12 such as a local area network (LAN). The main memory 3 is a device that stores the program which is executed by the CPU 2 or data during a computing process.

The display memory 5 temporarily stores display data which is displayed on the display device 6 such as a liquid crystal display or a cathode ray tube (CRT). The mouse 8 or the keyboard 9 is an operation device that is used for an operator to issue an operation instruction to the medical image processing device 1. The mouse 8 may be another pointing device such as a track pad or a track ball.

The controller 7 serves to detect a state of the mouse 8, to acquire a position of a mouse pointer on the display device 6, and to output acquired position information or the like to the CPU 2. The network adapter 10 is used to connect the medical image processing device 1 to the network 12 such as a LAN, a telephone line, or the Internet.

The medical image capturing device 13 is a device that acquires a medical image such as a tomographic image of an examinee. The medical image capturing device 13 is, for example, an X-ray CT device and will be described later with reference to FIG. 2. The medical image database 14 is a database system that stores medical images captured by the medical image capturing device 13.

Figure 2:
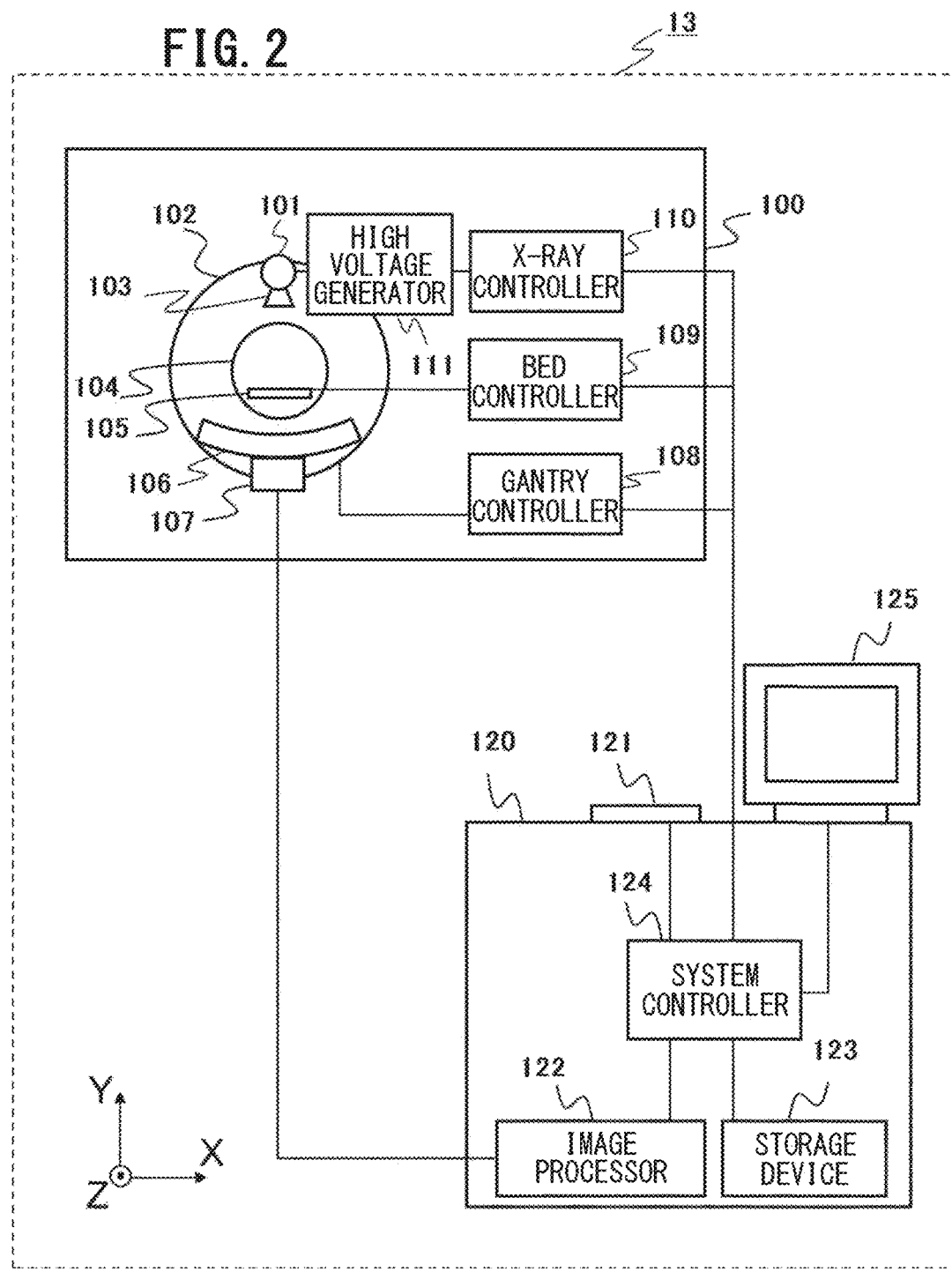
FIG. 2 is a diagram illustrating the whole configuration of an X-ray CT device which is an example of a medical image capturing device 13.

The whole configuration of an X-ray CT device which is an example of the medical image capturing device 13 will be described below with reference to FIG. 2. As illustrated in FIG. 2, the X-ray CT device includes a scan gantry unit 100 and an operation unit 120. The scan gantry unit 100 includes an X-ray tube device 101, a rotating disk 102, a collimator 103, an X-ray detector 106, a data collecting device 107, a bed device 105, a gantry controller 108, a bed controller 109, an X-ray controller 110, and a high voltage generator 111.

The X-ray tube device 101 is a device that irradiates an examinee placed on the bed device 105 with X-rays. The collimator 103 is a device that limits a radiation range of X-rays which are radiated from the X-ray tube device 101. The rotating disk 102 includes an opening 104 which an examinee placed on the bed device 105 enters, and rotates around the examinee with the X-ray tube device 101 and the X-ray detector 106 mounted thereon.

The X-ray detector 106 is a device that is disposed to face the X-ray tube device 101 and measures a spatial distribution of transmitted X-rays by detecting X-rays transmitted by the examinee, in which a plurality of X-ray detecting elements are arranged two-dimensionally in a circumferential direction and a rotation axis direction (a Z-axis direction) in a rotation plane (XY plane) of the rotating disk 102. The data collecting device 107 is a device that collects X-ray doses detected by the X-ray detector 106 as digital data.

The gantry controller 108 is a device that controls rotation of the rotating disk 102. The bed controller 109 is a device that controls upward, downward, leftward, rightward, forward, and rearward movements of the bed device 105. The high voltage generator 111 is a device that generates a high voltage which is applied to the X-ray tube device 101. The X-ray controller 110 is a device that controls the output of the high voltage generator 111.

The operation unit 120 includes an input device 121, an image processor 122, a display device 125, a storage device 123, and a system controller 124. The input device 121 is a device that is used to input an examinee name, examination date and time, scan conditions, and the like and is specifically a keyboard or a pointing device. The image processor 122 is a device that processes projection data transmitted from the data collecting device 107 and reconstructs a CT image.

The display device 125 is a device that displays the CT image generated by the image processor 122 and is specifically a liquid crystal display or the like. The storage device 123 is a device that stores data collected by the data collecting device 107 and image data of the CT image generated by the image processor 122 and is specifically a hard disk drive (HDD) or the like. The system controller 124 is a device that controls these devices, the gantry controller 108, the bed controller 109, and the X-ray controller 110.

By causing the X-ray controller 110 to control the high voltage generator 111 on the basis of scan conditions input from the input device 121, particularly, a tube voltage, a tube current, and the like, predetermined power is supplied to the X-ray tube device 101 from the high voltage generator 111. The X-ray tube device 101 irradiates an examinee with X-rays based on the scan conditions with the supplied power. The X-ray detector 106 detects X-rays which are radiated from the X-ray tube device 101 and transmitted by the examinee using a plurality of X-ray detecting elements and measures a distribution of transmitted X-rays. The rotating disk 102 is controlled by the gantry controller 108 and rotates on the basis of the scan conditions input from the input device 121, particularly, a rotation speed or the like. The bed device 105 is controlled by the bed controller 109 and operates on the basis of the scan conditions input from the input device 121, particularly, a helical pitch or the like.

By repeating irradiation with X-rays from the X-ray tube device 101 and measurement of a transmitted X-ray distribution by the X-ray detector 106 along with rotation of the rotating disk 102, projection data at various angles is acquired. The projection data is correlated with a view indicating each angle and a channel (ch) number and a row number which are the number of a detecting element of the X-ray detector 106. The acquired projection data at various angels is transmitted to the image processor 122. The image processor 122 reconstructs a CT image by performing a back projection process on the transmitted projection data at various angles. The CT image acquired by reconstruction is displayed on the display device 125.

The operation unit 120 may be the medical image processing device 1 which has been described above with reference to FIG. 1. In this case, the system controller 124 corresponds to the CPU 2, the main memory 3, and the display memory 5, the storage device 123 corresponds to the storage device 4, the input device 121 corresponds to the controller 7, the mouse 8, and the keyboard 9, and the display device 125 corresponds to the display device 6.

Figure 3:
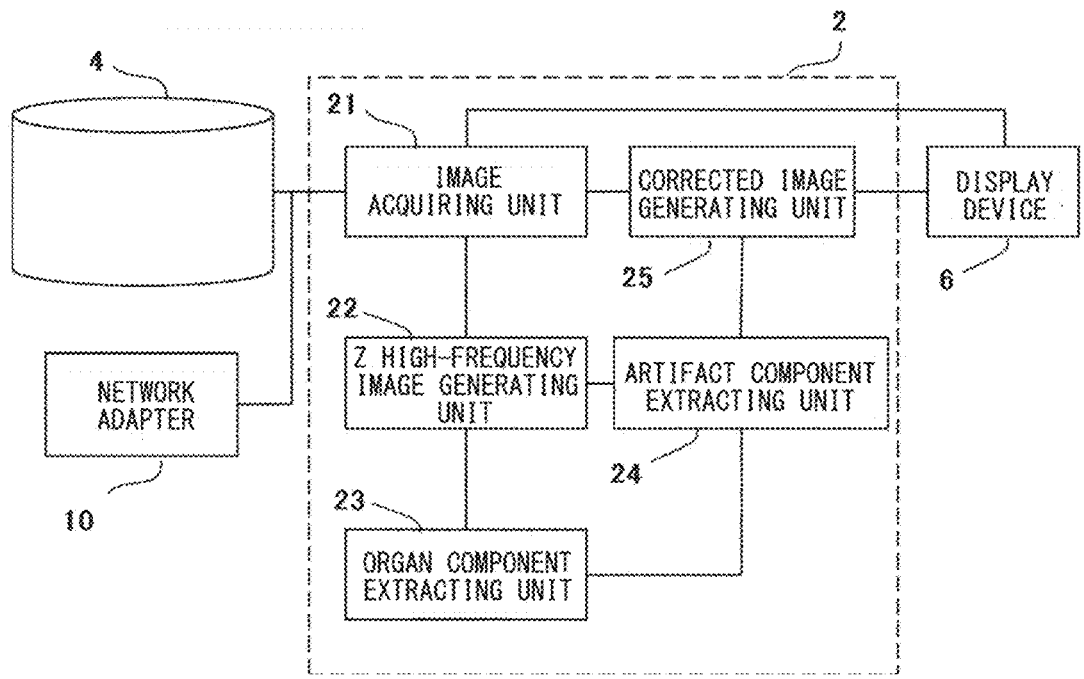
FIG. 3 is a functional block diagram illustrating a first embodiment.

Principal parts in this embodiment will be described below with reference to FIG. 3. These principal parts may be embodied in dedicated hardware or may be embodied in software which operates in the CPU 2. In the following description, it is assumed that the principal parts in this embodiment are embodied in software.

The principal parts in this embodiment include an image acquiring unit 21, a Z high-frequency image generating unit 22, an organ component extracting unit 23, an artifact component extracting unit 24, and a corrected image generating unit 25. A 3D volumetric image is stored in the storage device 4. A 3D volumetric image is an image which is obtained by stacking a plurality of tomographic images acquired by the medical image capturing device 13 in the rotation axis direction or an image which is obtained by cone beam reconstruction such as Feldkamp reconstruction. In this embodiment, a 3D volumetric image including a windmill artifact which is generated due to under-sampling in the rotation axis direction is a main target. The elements will be described below.

The image acquiring unit 21 acquires a 3D volumetric image. The 3D volumetric image may be acquired from the storage device 4 or may be acquired from the medical image capturing device 13 or the medical image database 14 via the network adapter 10. The 3D volumetric image acquired by the image acquiring unit 21 may be displayed on the display device 6.

The Z high-frequency image generating unit 22 generates a Z high-frequency image which is a high-frequency component in the rotation axis direction from the 3D volumetric image. The Z high-frequency image includes an organ component indicating a shape of an organ in an examinee in addition to a windmill artifact.

The windmill artifact is an artifact having a windmill blade shape including a pair of black and white, and the number of blades or the artifact intensity varies depending on a helical pitch. That is, as the helical pitch increases, the number of blades increase but the artifact intensity decrease. In the windmill artifact, a position in the rotating direction at which a blade appears in a plane perpendicular to the rotation axis changes when the position in the rotation axis direction changes. The position in the rotating direction at which a blade appears is also affected by a reconstruction slice thickness or a reconstruction slice interval. In this way, the position or intensity in which the windmill artifact appears varies depending on scan conditions or reconstruction conditions.

The organ component extracting unit 23 extracts an organ component from the Z high-frequency image. Since the windmill artifact is an artifact which is generated due to under-sampling in the rotation axis direction, the windmill artifact can be markedly reduced by a smoothing process in the rotation axis direction. On the other hand, even when the smoothing process in the rotation axis direction is performed, the boundary of the organ component becomes slightly unclear but the organ component is maintained. The organ component extracting unit 23 extracts the organ component using such a difference between the windmill artifact and the organ component.

The artifact component extracting unit 24 extracts an artifact component on the basis of the Z high-frequency image and the organ component. Since the Z high-frequency image includes an organ component in addition to a windmill artifact which is an artifact component, the artifact component extracting unit 24 extracts the artifact component on the basis of a result obtained by subtracting the organ component from the Z high-frequency image.

The corrected image generating unit 25 generates a corrected image by subtracting the artifact component from the 3D volumetric image. By subtracting the artifact component from the 3D volumetric image including the windmill artifact, the corrected image generating unit 25 generates a corrected image in which the windmill artifact has been reduced.

Figure 4:
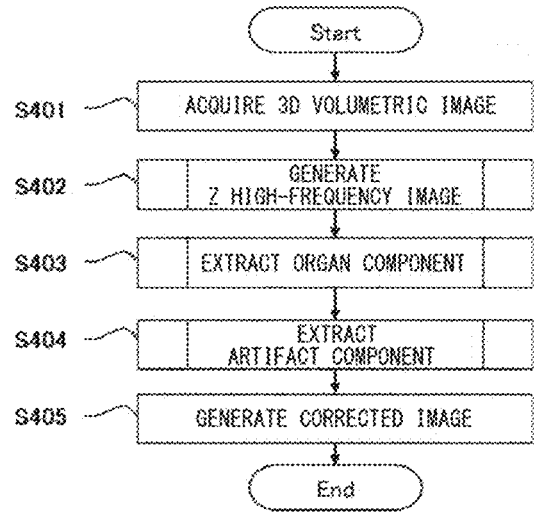
FIG. 4 is a diagram illustrating a process flow in the first embodiment.
Figure 8E:
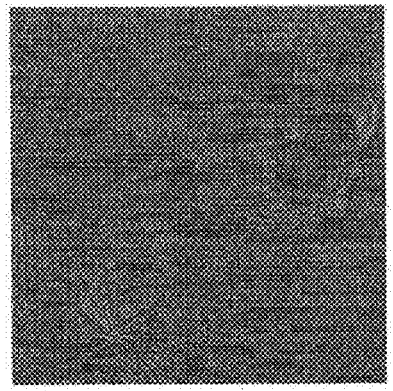
FIG. 8 is a first diagram illustrating a result of effect verification in the first embodiment.
Figure 8C:
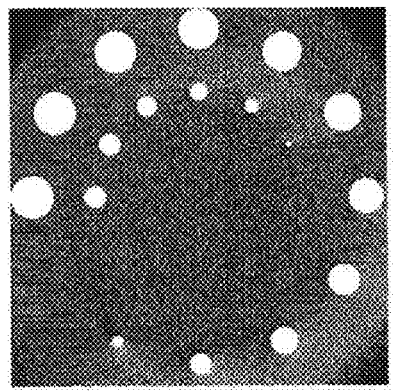
Figure 8D:
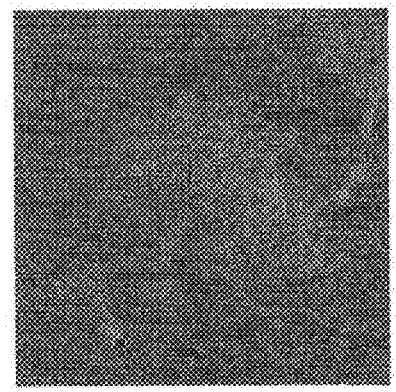
Figure 8B:
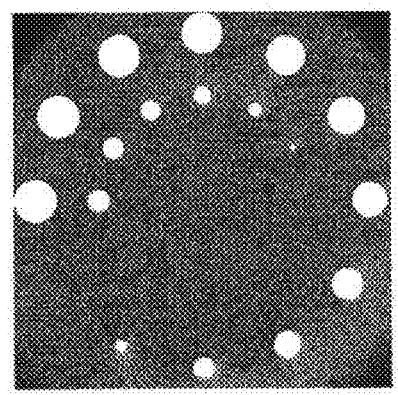
Figure 8A:
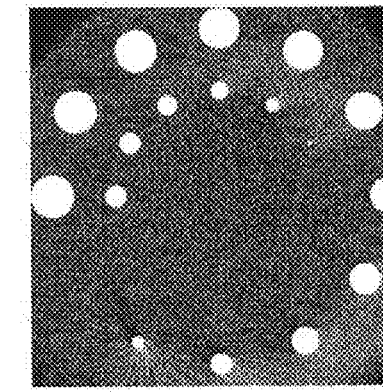
Figure 9A:
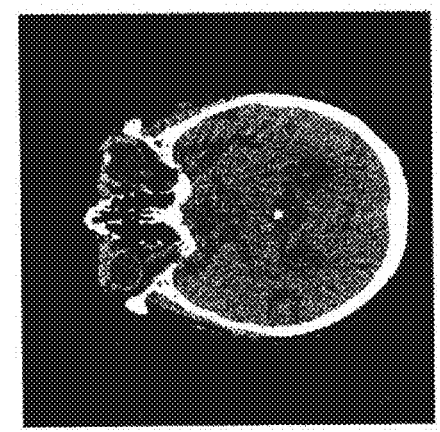
FIG. 9 is a second diagram illustrating a result of effect verification in the first embodiment.
Figure 9B:
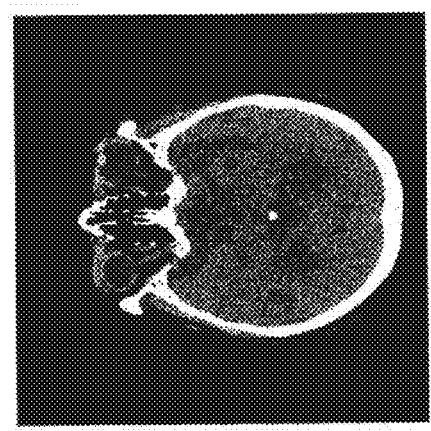
Figure 9D:
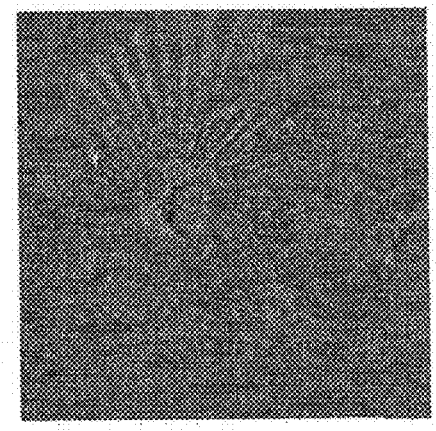
Figure 9C:
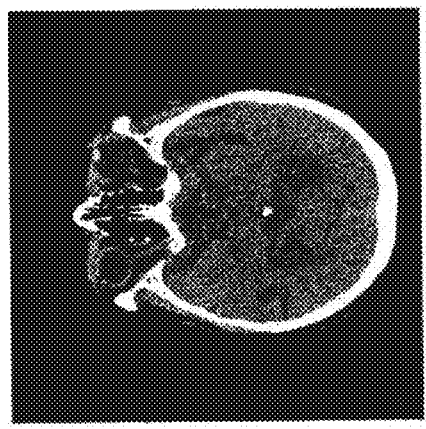
Figure 9E:
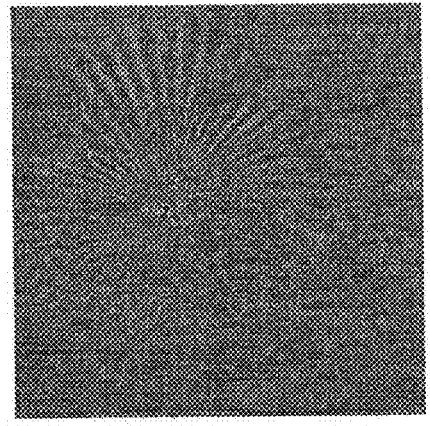
Figure 10E:
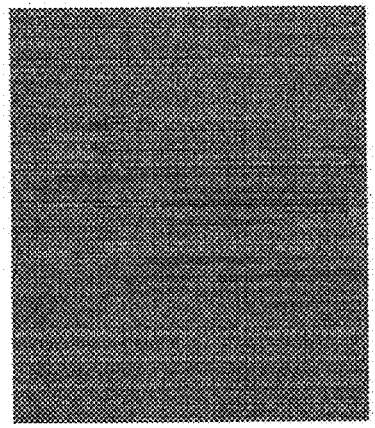
FIG. 10 is a third diagram illustrating a result of effect verification in the first embodiment.
Figure 10C:
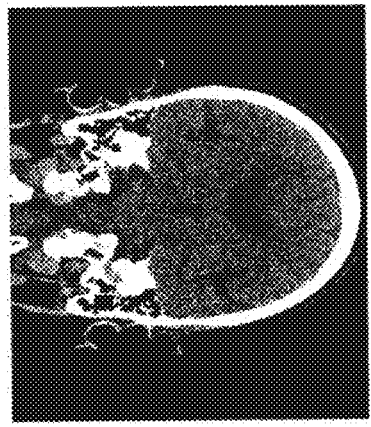
Figure 10D:
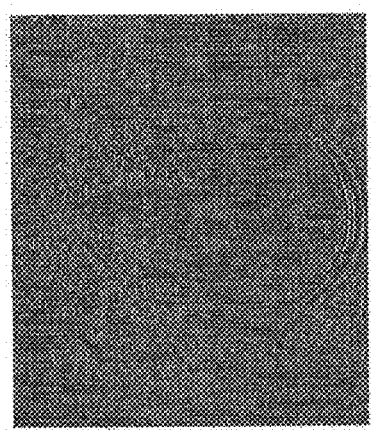
Figure 10B:
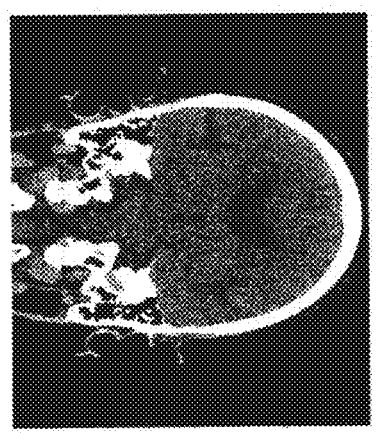
Figure 10A:
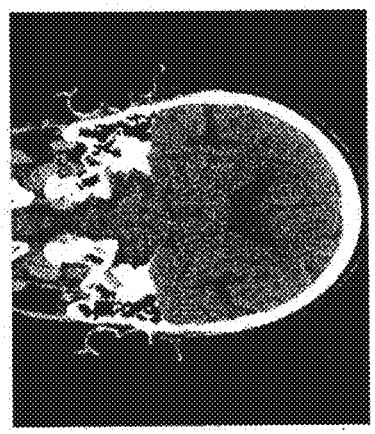

A process flow which is performed by the medical image processing device 1 including the above-mentioned constituent units will be described below with reference to FIG. 4.

(S401)

The image acquiring unit 21 acquires a 3D volumetric image. The 3D volumetric image may be acquired from the storage device 4 or may be acquired from the medical image capturing device 13 or the medical image database 14 via the network adapter 10. The acquired 3D volumetric image is transmitted to the Z high-frequency image generating unit 22 and the corrected image generating unit 25.

(S402)

The Z high-frequency image generating unit 22 generates a Z high-frequency image from the 3D volumetric image. A process flow of generating a Z high-frequency image in this embodiment will be described below with reference to FIG. 5.

(S501)

The Z high-frequency image generating unit 22 generates a Z image which is an image in the rotation axis (Z) direction from the 3D volumetric image. The Z image is a set of lines including voxels which are arranged in the rotation axis (Z) direction in the 3D volumetric image at an arbitrary coordinate in a plane perpendicular to the rotation axis.

(S502)

The Z high-frequency image generating unit 22 performs a smoothing process on the Z image in the rotation axis (Z) direction. As the result of the smoothing process, a Z smoothed image is acquired as an image which is obtained by performing the smoothing process on the Z image in the rotation axis (Z) direction. It is desirable that an edge-preserved smoothing filter such as a total variation (TV) filter be used for the smoothing process of this step. The smoothing filter which is used in this embodiment is a one-dimensional filter which is applied in the rotation axis (Z) direction. By employing the edge-preserved smoothing filter, it is possible to perform subsequent processes while maintaining a boundary of an organ.

(S503)

The Z high-frequency image generating unit 22 substrates the Z smoothed image from the Z image. By subtracting the Z smoothed image from the Z image, a Z high-frequency image which is a high-frequency component in the Z image is generated. The Z high-frequency image is transmitted to the organ component extracting unit 23 and the artifact component extracting unit 24.

(S403)

The organ component extracting unit 23 extracts an organ component from the Z high-frequency image. A process flow of extracting an organ component in this embodiment will be described below with reference to FIG. 6.

(S601)

The organ component extracting unit 23 acquires the Z high-frequency image.

(S602)

The organ component extracting unit 23 performs a smoothing process on the Z high-frequency image in the rotation axis (Z) direction. As the result of the smoothing process, an organ component is extracted. It is desirable that a filter having greater smoothing strength than that of the edge-preserved smoothing filter such as a Gaussian filter or a simple averaging filter be used for the smoothing process of this step. By employing a filter having great smoothing strength, an artifact component can be markedly reduced and an organ is maintained while the boundary thereof is slightly unclear. The extracted organ component is transmitted to the artifact component extracting unit 24.

The smoothing strength of the smoothing filter which is used for the smoothing process of this step may change depending on the scan conditions or reconstruction conditions which have been used to generate the 3D volumetric image. The number or position of blades of a windmill artifact or artifact intensity included in the 3D volumetric image differs depending on the scan conditions or the reconstruction conditions. Accordingly, it is preferable that the smoothing strength of the smoothing filter change depending on the scan conditions or the reconstruction conditions.

For example, it is preferable that the smoothing strength change to be less as the helical pitch in the scan conditions becomes less. It is also preferable that the smoothing strength change to be less as the reconstruction slice thickness in the reconstruction conditions becomes greater. It is also preferable that the smoothing strength change to be greater as an X-ray absorption coefficient of an organ which is an observation target becomes greater. It is also preferable that the smoothing strength change to be greater as image noise becomes greater as in a case in which an X-ray dose is small or a reconstruction filter that enhances a high frequency is used.

(S404)

The artifact component extracting unit 24 extracts an artifact component on the basis of the Z high-frequency image and the organ component. A process flow of extracting an artifact component in this embodiment will be described below with reference to FIG. 7.

(S701)

The artifact component extracting unit 24 acquires a Z high-frequency image and an organ component.

(S702)

The artifact component extracting unit 24 subtracts the organ component from the Z high-frequency image. Since the Z high-frequency image includes the organ component in addition to an artifact component, the artifact component is extracted by subtracting the organ component from the Z high-frequency image. The extracted artifact component is transmitted to the corrected image generating unit 25.

(S405)

The corrected image generating unit 25 generates a corrected image by subtracting the artifact component from the 3D volumetric image. Since the organ component has been subtracted from the Z high-frequency image and the artifact component has been extracted through the previous steps, a corrected image in which the artifact component is reduced while the organ component is maintained is generated. The generated corrected image is displayed on the display device 6.

Through the above-mentioned process flows, it is possible to reduce a windmill artifact from a 3D volumetric image. Particularly, it is possible to reduce even a windmill artifact including a high-frequency component in a plane perpendicular to the rotation axis and to make a boundary of an organ clear to maintain the contrast.

A result of effect verification in this embodiment will be described below by comparison with the related art with reference to FIGS. 8 to 10.

FIG. 8 illustrates an original image acquired by scanning a phantom in which spheres having different sizes are arranged and corrected images acquired according to the related art and this embodiment for comparison. Tomographic images of the corrected images according to the related art and the embodiment and the original image are illustrated in FIGS. 8 (a) to 8 (c), and subtracted images acquired by subtracting the original image from the corrected images according to the related art and the embodiment are illustrated in FIGS. 8 (d) and 8 (e).

In the tomographic image of the original image (FIG. 8 (a)), a windmill artifact is conspicuous around a left-upper sphere and a right-lower inside sphere. In the tomographic image according to the related art (FIG. 8 (b)), the windmill artifacts are reduced but a high-frequency component remains. On the other hand, in the tomographic image according to this embodiment (FIG. 8 (c)), a windmill artifact of a high-frequency component is also reduced.

This is clear from the subtracted image. A windmill artifact of a lower-frequency component appears in the subtracted image illustrated in FIG. 8 (d) according to the related art, but a windmill artifact of a high-frequency component as well as a low-frequency component appears in the subtracted image illustrated in FIG. 8 (e) according to this embodiment. A boundary of a sphere appears in the subtracted image illustrated in FIG. 8 (d) according to the related art, but a boundary of a sphere is not conspicuous in this embodiment (FIG. 8 (e)). That is, it can be seen that a boundary of an organ which may be unclear in the related art can be maintained in this embodiment.

Images obtained by scanning a head phantom are illustrated in FIGS. 9 and 10 similarly to FIG. 8. In the original image of a head image 1 in FIG. 9 (a), an artifact appears on the right-upper side. An artifact is reduced but is not sufficient in the related art (FIG. 9 (b)), but an artifact is further reduced in this embodiment (FIG. 9 (c)). In the subtracted images, a bone boundary appearing in the related art of FIG. 9 (d) does not appear in this embodiment of FIG. 9 (e).

In the original image of a head image 2 in FIG. 10 (a), a conspicuous artifact does not appear. Any new artifact does not appear in corrected image of the related art (FIG. 10 (b)) and in this embodiment (FIG. 10 (c)). On the other hand, in the subtracted images, an organ boundary appearing in the related art of FIG. 10 (d) does not appear in this embodiment of FIG. 10 (e).

According to this embodiment, it can be seen from the above-mentioned result of comparison that it is possible to reduce even a windmill artifact including a high-frequency component in a plane perpendicular to the rotation axis and to make a boundary of an organ clear to maintain the contrast.

Second Embodiment

A second embodiment will be described below. This embodiment is almost the same as the first embodiment but is different from the first embodiment in a process flow of generating a Z high-frequency image from a 3D volumetric image, that is, S402 in FIG. 4. The process flow of S402 in this embodiment will be described below with reference to FIG. 11.

(S1101)

The Z high-frequency image generating unit 22 generates a first planar image which is an image in a first plane which is a plane along to the rotation axis (Z) direction from a 3D volumetric image. The first planar image is, for example, a coronal image or a sagittal image.

(S1102)

The Z high-frequency image generating unit 22 performs a smoothing process on the first planar image in the rotation axis (Z) direction. As the result of the smoothing process, a first planar smoothed image is acquired as an image obtained by performing a smoothing process on the first planar image in the rotation axis (Z) direction. It is desirable that an edge-preserved smoothing filter such as a total variation (TV) filter be used for the smoothing process of this step. The smoothing filter which is used in this embodiment is a two-dimensional filter which is applied along the first plane. By employing the edge-preserved smoothing filter, it is possible to perform subsequent processes while maintaining a boundary of an organ component.

(S1103)

The Z high-frequency image generating unit 22 subtracts the first planar smoothed image from the first planar image. By subtracting the first planar smoothed image from the first planar image, a first planar high-frequency image which is a high-frequency component in the first planar image is generated.

(S1104)

The Z high-frequency image generating unit 22 generates a second planar image which is an image in a second plane which is a plane along to the rotation axis (Z) direction and a plane perpendicular to the first plane from the first planar high-frequency image. The second planar image is a sagittal image, for example, when the first planar image is a coronal image and is a coronal image when the first planar image is a sagittal image.

(S1105)

The Z high-frequency image generating unit 22 performs a smoothing process on the second planar image in the rotation axis (Z) direction. As the result of the smoothing process, a second planar smoothed image is acquired as an image obtained by performing the smoothing process on the second planar image in the rotation axis (Z) direction. Similarly to S1102, it is desirable that an edge-preserved smoothing filter be used for the smoothing process of this step. The smoothing filter which is used in this embodiment is a two-dimensional filter which is applied along the second plane. By employing the edge-preserved smoothing filter, it is possible to perform subsequent processes while maintaining a boundary of an organ component.

(S1106)

The Z high-frequency image generating unit 22 subtracts the second planar smoothed image from the second planar image. By subtracting the second planar smoothed image from the second planar image, a second planar high-frequency image which is a high-frequency component in the second planar image is generated. The generated second planar high-frequency image is transmitted as a Z high-frequency image to the organ component extracting unit 23 and the artifact component extracting unit 24.

Through the above-mentioned process flows, similarly to the first embodiment, the organ component extracting unit 23 and the artifact component extracting unit 24 acquire the Z high-frequency image. Since the subsequent process flows are the same as in the first embodiment, it is also possible to reduce a windmill artifact from a 3D volumetric image in this embodiment, similarly to the first embodiment. In addition, it is possible to reduce even a windmill artifact including a high-frequency component in a plane perpendicular to the rotation axis and to make a boundary of an organ clear to maintain the contrast.

Third Embodiment

A third embodiment will be described below. This embodiment is also almost the same as the first embodiment but is different from the first embodiment in a process flow of extracting an organ component from a Z high-frequency image, that is, S403 in FIG. 4. The process flow of S403 in this embodiment will be described below with reference to FIG. 12.

(S1201)

The organ component extracting unit 23 acquires a Z high-frequency image.

(S1202)

The organ component extracting unit 23 performs a threshold value process on the Z high-frequency image. In the threshold value process of this step, a pixel value of a pixel of which a pixel value is greater than a threshold value in the Z high-frequency image is converted to a pixel value equal to or less than the threshold value, for example, an average value of pixel values of neighboring pixels of a target pixel or zero. The threshold value may be determined in advance or may be input by an operator via the keyboard 9 or the like. By performing the threshold value process, a boundary of an organ is more easily maintained in the subsequent processes. An image obtained through the threshold value process is sent to a next step as a converted Z high-frequency image.

(S1203)

The organ component extracting unit 23 performs a smoothing process on the converted Z high-frequency image in the rotation axis (Z) direction. As the result of the smoothing process, an organ component is extracted. Similarly to the first embodiment, it is desirable that a filter having greater smoothing strength than that of the edge-preserved smoothing filter be used for the smoothing process of this step. By employing a filter having great smoothing strength, an artifact component can be markedly reduced and an organ component is maintained while the boundary thereof is slightly unclear. The extracted organ component is transmitted to the artifact component extracting unit 24.

Through the above-mentioned process flows, the artifact component extracting unit 24 acquires an organ component similarly to the first embodiment. Particularly, since the smoothing process is performed after the threshold value process has been performed on the Z high-frequency image, the organ component is more clearly extracted.

Since the subsequent process flows are the same as in the first embodiment, it is also possible to reduce a windmill artifact from a 3D volumetric image in this embodiment, similarly to the first embodiment. In addition, it is possible to reduce even a windmill artifact including a high-frequency component in a plane perpendicular to the rotation axis and to make a boundary of an organ clearer to maintain the contrast.

Fourth Embodiment

Figure 13:
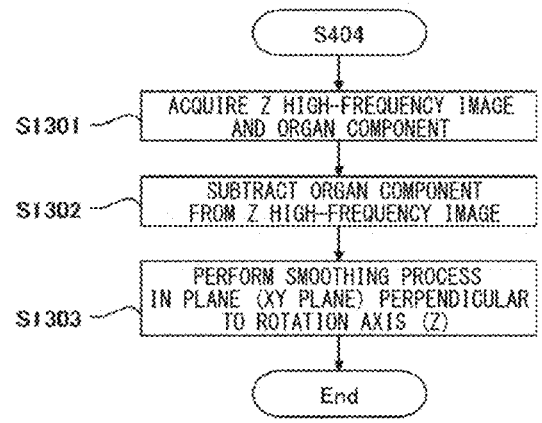
FIG. 13 is a diagram illustrating a process flow of S404 in a fourth embodiment.

A fourth embodiment will be described below. This embodiment is also almost the same as the first embodiment but is different from the first embodiment in a process flow of extracting an artifact component from a Z high-frequency image, that is, S404 in FIG. 4. The process flow of S404 in this embodiment will be described below with reference to FIG. 13.

(S1301)

The artifact component extracting unit 24 acquires a Z high-frequency image and an organ component.

(S1302)

The artifact component extracting unit 24 subtracts the organ component from the Z high-frequency image. The subtraction result is extracted as a first artifact component.

(S1303)

The artifact component extracting unit 24 performs a smoothing process on the organ component along a plane perpendicular to the rotation axis. The result of the smoothing process is extracted as a second artifact component. For example, a Gaussian filter or a TV filter is used for the smoothing process of this step. A cone beam artifact component may be included in the organ component. In this step, the cone beam artifact component is extracted as the second artifact component by performing the smoothing process on the organ component along the plane perpendicular to the rotation axis.

The artifact component extracting unit 24 adds or weighting-adds the first artifact component and the second artifact component. The addition result is transmitted as an artifact component to the corrected image generating unit 25.

Through the above-mentioned process flows, similarly to the first embodiment, the corrected image generating unit 25 acquires the artifact component. Particularly, the second artifact component which is a cone beam artifact component is extracted in addition to the first artifact component.

Since the subsequent process flows are the same as in the first embodiment, it is also possible to reduce a windmill artifact from a 3D volumetric image in this embodiment, similarly to the first embodiment. In addition, it is possible to reduce even a windmill artifact including a high-frequency component in a plane perpendicular to the rotation axis and to make a boundary of an organ clear to maintain the contrast. Even when a cone beam artifact component is included in a 3D volumetric image, it is possible to reduce such an artifact component.

Fifth Embodiment

Figure 14:
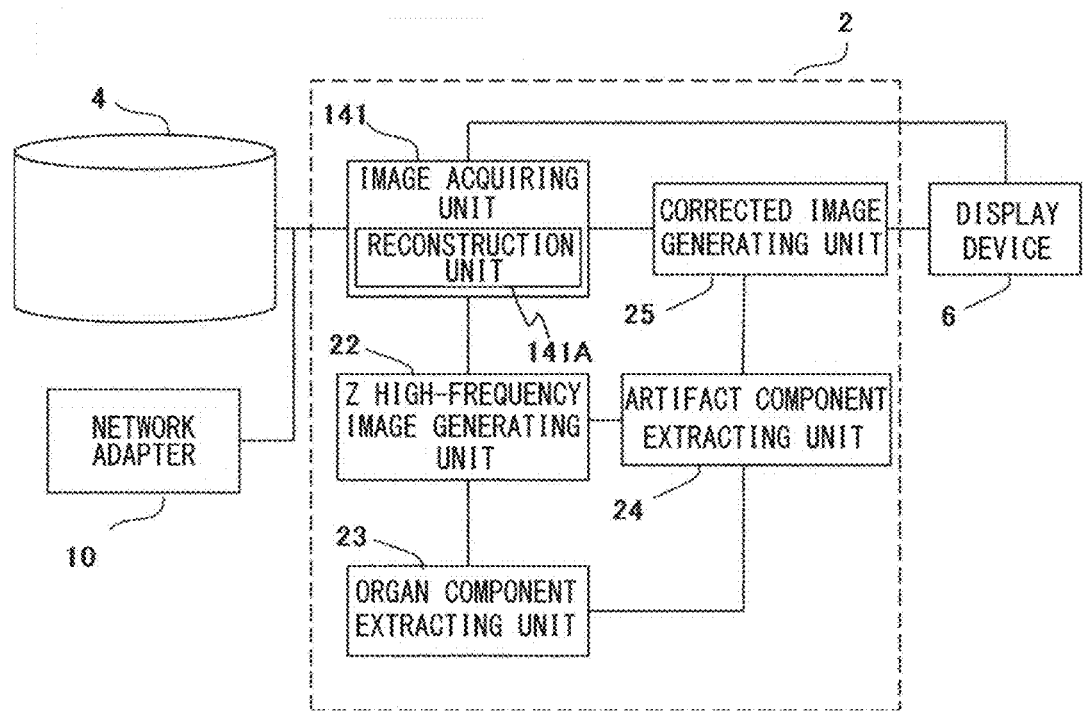
FIG. 14 is a functional block diagram illustrating a fifth embodiment.

A fifth embodiment will be described below. This embodiment is also almost the same as the first embodiment but is different from the first embodiment in that a 3D volumetric image is acquired again if necessary, that is, in the configuration of the image acquiring unit 21 in FIG. 3. An image acquiring unit 141 in this embodiment will be described below with reference to FIG. 14.

The image acquiring unit 141 includes a reconstruction unit 141A that generates a tomographic image by reconstructing projection data. When the acquired 3D volumetric image is not suitable for the processes subsequent to S402 in FIG. 4, the reconstruction unit 141A performs a reconstruction process with reconstruction conditions changed and generates a 3D volumetric image again.

As described above, the position in the rotating direction in which a blade of a windmill artifact appears is affected by the helical pitch and the reconstruction slice interval. The position in the rotating direction in which a blade appears may be provided at a neighboring position on the rotation axis under a certain condition. In this case, the windmill artifact does not include a high-frequency component in the rotation axis direction and a 3D volumetric image which is not suitable for the processes subsequent to S402 in FIG. 4 is acquired.

Therefore, when the position in the rotating direction in which a blade appears is provided at a neighboring position on the rotation axis, the image acquiring unit 141 according to this embodiment causes the reconstruction unit 141A to change the reconstruction conditions and to perform a reconstruction process. For example, the reconstruction unit 141A performs the reconstruction process in a state in which the reconstruction slice interval has been changed to be less than the original reconstruction slice interval and generates a 3D volumetric image again. Alternatively, the reconstruction unit 141A adds a reconstruction process at a reconstruction slice position which is newly set between the original reconstruction slice positions and generates a 3D volumetric image again. Since the 3D volumetric image, which is generated again, includes a high-frequency component of a windmill artifact in the rotation axis direction, the processes subsequent to S402 in FIG. 4 work more effectively.

The reconstruction unit 141A may change the reconstruction slice thickness to be less than the original reconstruction slice thickness and generate a 3D volumetric image again. At this time, a high frequency enhancing process may be performed in the rotation axis direction. By employing this configuration, a boundary of an organ in the corrected image acquired in S405 in FIG. 4 is made to be clearer in the rotation axis direction.

The image acquiring unit 141 may include a reconstruction instructing unit that instructs the image processor 122 of the X-ray CT device to perform a reconstruction process instead of the reconstruction unit 141A. The reconstruction instructing unit causes the image processor 122 to perform a reconstruction process under the changed reconstruction conditions and the image acquiring unit 141 acquires a 3D volumetric image which is obtained as a result.

Since the subsequent process flows are the same as in the first embodiment, it is also possible to reduce a windmill artifact from a 3D volumetric image in this embodiment, similarly to the first embodiment. In addition, it is possible to reduce even a windmill artifact including a high-frequency component in a plane perpendicular to the rotation axis and to make a boundary of an organ clear to maintain the contrast.

The medical image processing device according to the invention is not limited to the above-mentioned embodiments and can be embodied by modifying elements thereof without departing from the gist of the invention. A plurality of elements disclosed in the above-mentioned embodiments may be appropriately combined. Some elements may be deleted from all the elements described in the above-mentioned embodiments.

REFERENCE SIGNS LIST

1 Medical image processing device
2 CPU
3 Main memory
4 Storage device
5 Display memory
6 Display device
7 Controller
8 Mouse
9 Keyboard
10 Network adapter
11 System bus
12 Network
13 Medical image capturing device
14 Medical image database
100 Scan gantry unit
101 X-ray tube device
102 Rotating disk
103 Collimator
104 Opening
105 Bed device
106 X-ray detector
107 Data collecting device
108 Gantry controller
109 Bed controller
110 X-ray controller
111 High voltage generator
120 Operation unit
121 Input device
122 Image processor
123 Storage device
124 System control device
125 Display device
21 Image acquiring unit
22 Z high-frequency generating unit
23 Organ component extracting unit
24 artifact component extracting unit
25 Corrected image generating unit
141 Image acquiring unit
141A Reconstruction unit

The invention claimed is:

1. A medical image processing device comprising:
an image acquirer that acquires a 3D volumetric image;
a Z high-frequency image generator that generates a Z high-frequency image which is a high-frequency component in a rotation axis direction from the 3D volumetric image;
an organ component extractor that extracts an organ component from the Z high-frequency image;
an artifact component extractor that extracts an artifact component on the basis of the Z high-frequency image and the organ component; and
a corrected image generator that generates a corrected image by subtracting the artifact component from the 3D volumetric image.

2. The medical image processing device according to claim 1, wherein the organ component extractor extracts the organ component by performing a smoothing process on the Z high-frequency image in the rotation axis direction.

3. The medical image processing device according to claim 2, wherein the Z high-frequency image generator generates a Z image which is an image in the rotation axis direction from the 3D volumetric image and generates the Z high-frequency image by subtracting a Z smoothed image which is an image obtained by performing a smoothing process on the Z image in the rotation axis direction from the Z image, and
wherein smoothing strength for generating the Z smoothed image is less than smoothing strength in the organ component extractor.

4. The medical image processing device according to claim 3, wherein the smoothing strength in the organ component extractor changes depending on scan conditions or reconstruction conditions which are used to generate the 3D volumetric image.

5. The medical image processing device according to claim 4, wherein the smoothing strength in the organ component extractor changes to become less as a helical pitch in the scan conditions becomes less.

6. The medical image processing device according to claim 4, wherein the smoothing strength in the organ component extractor changes to become less as a reconstruction slice thickness in the reconstruction conditions becomes larger.

7. The medical image processing device according to claim 2, wherein the Z high-frequency image generator generates a first planar image which is an image in a first plane which is a plane along to the rotation axis direction from the 3D volumetric image and generates a first planar high-frequency image by subtracting a first planar smoothed image which is an image obtained by performing a smoothing process on the first planar image in the rotation axis direction from the first planar image,
wherein the Z high-frequency image generator generates a second planar image which is an image in a second plane which is a plane along to the rotation axis direction and perpendicular to the first plane from the first planar high-frequency image and generates the Z high-frequency image by subtracting a second planar smoothed image which is an image obtained by performing a smoothing process on the second planar image in the rotation axis direction from the second planar image, and wherein smoothing strength for generating the first planar smoothed image and the second planar smoothed image is less than smoothing strength in the organ component extractor.

8. The medical image processing device according to claim 1, wherein the artifact component extractor extracts the artifact component by subtracting the organ component from the Z high-frequency image.

9. The medical image processing device according to claim 1, wherein the organ component extractor converts a pixel value of a pixel of which the pixel value is higher than a threshold value in the Z high-frequency image into a pixel value equal to or less than the threshold value to generate a converted Z high-frequency image and extracts the organ component by performing a smoothing process on the converted Z high-frequency image in the rotation axis direction.

10. The medical image processing device according to claim 1, wherein the artifact component extractor extracts the artifact component by adding a result obtained by performing a smoothing process on the organ component along a plane perpendicular to the rotation axis to a result obtained by subtracting the organ component from the Z high-frequency image.

11. The medical image processing device according to claim 1, wherein the image acquirer is configured to acquire the 3D volumetric image again.

12. An X-ray CT device comprising the medical image processing device according to claim 1.

13. A medical image processing method comprising:
an image acquiring step of acquiring a 3D volumetric image;
a Z high-frequency image generating step of generating a Z high-frequency image which is a high-frequency component in a rotation axis direction from the 3D volumetric image;
an organ component extracting step of extracting an organ component from the Z high-frequency image;
an artifact component extracting step of extracting an artifact component on the basis of the Z high-frequency image and the organ component; and
a corrected image generating step of generating a corrected image by subtracting the artifact component from the 3D volumetric image.

* * * * *